United States Patent [19] [11] 4,003,948
Yamashita et al. [45] Jan. 18, 1977

[54] PROCESS FOR PREPARING DIMETHYL 2,6-NAPHTHALENEDICARBOXYLATE

[75] Inventors: Gentaro Yamashita; Nobuo Taneda; Kiyoshi Yamamoto; Toru Matsubayashi; Hiromitsu Takamoto, all of Iwakuni, Japan

[73] Assignee: Teijin Limited, Osaka, Japan

[22] Filed: Mar. 4, 1975

[21] Appl. No.: 555,125

[30] Foreign Application Priority Data
Oct. 2, 1974 Japan ............................ 49-112822
Mar. 8, 1974 Japan ............................ 49-26338

[52] U.S. Cl. ....................................... 260/475 FR
[51] Int. Cl.² ........................................ C07C 69/76
[58] Field of Search ............................ 260/475 FR

[56] References Cited
UNITED STATES PATENTS 3,431,243 3/1969 Uno et al. ...................... 260/475 P
3,655,729 4/1972 Rinehart ........................ 260/475 P Primary Examiner—Jane S. Myers
Attorney, Agent, or Firm—Sherman & Shalloway

[57] ABSTRACT

A process for preparing dimethyl 2,6-naphthalenedicarboxylate, which comprises continuously esterifying 2,6-naphthalenedicarboxylic acid with methanol at a temperature of about 140° to about 350° C. in the presence or absence of an esterifying catalyst, said 2,6-naphthalenedicarboxylic acid being fed into an esterification reaction zone in the form of solid particles having a specific surface area of about 4,000 cm²/g.

7 Claims, 3 Drawing Figures

BLAINE AIR-PERMEATING DEVICE

PROCESS FOR PREPARING DIMETHYL 2,6-NAPHTHALENEDICARBOXYLATE

This invention relates to a process for preparing dimethyl 2,6-naphthalenedicarboxylate [2,6-NDA·(CH$_3$)$_2$ for short] which comprises continuously esterifying 2,6-naphthalenedicarboxylic acid (2,6-NDA for short) with methanol at a temperature of about 140° to about 350° C. and an elevated pressure in the presence or absence of an esterifying catalyst, said 2,6-naphthalenedicarboxylic acid being fed into an esterification reaction zone in the form of solid particles having a specific surface area of about 4,000 cm$^2$/g.

By using 2,6-NDA as solid particles having a certain specific surface area, blockage phenomena occurring in starting suspensions, feed lines and reaction vessels during the esterification of 2,6-NDA in the form of a suspension can be prevented, and the esterification reaction can be continuously performed over long periods of time in good condition and with operational advantages. Furthermore, according to the process of this invention, the use of an esterification catalyst such as inorganic acids (e.g., sulfuric acid) can be omitted, and therefore, the esterification reaction can be performed without operational disadvantages ascribable to the use of catalyst, such as the corrosion of the reaction equipment, the reduction of the purity of the product or the need for a step of separating the catalyst. In addition, products of superior quality can be obtained in good yields.

Dimethyl 2,6-naphthalenedicarboxylate is useful as a raw material for preparing polyalkylene-2,6-naphthalates which are polyesters having superior properties. It is known that in the preparation of a dimethyl ester of an aromatic dicarboxylic acid, the aromatic dicarboxylic acid is reacted with methanol at the esterification temperature in the presence or absence of an esterifying catalyst.

One known method for esterifying 2,6-naphthalenedicarboxylic acid comprises reacting it with methanol in the liquid phase at a relatively low temperature of 110° to 220° C. in the presence of a naphthalene derivative such as dimethyl 2,6-naphthalenedicarboxylate (see U.S. Pat. No. 3,042,709). In order to perform the esterification at a feasible rate of reaction, however, this method requires the use of an acid catalyst such as sulfuric acid. This naturally induces a side reaction which converts methanol to its dimethyl ether, and results in the disadvantage of wasting methanol. Furthermore, according to this method, a reaction apparatus is required which can fully withstand the corrosive attack of the acid catalyst, and also the method has the disadvantage that undesirable colored components or other difficultly-separable by-products occur in the reaction product. Still another disadvantage is that the catalyst remaining in the product is difficult to separate and remove.

On the other hand, in the preparation of dimethyl terephthalate, it has been the practice to feed a suspension of solid particles of terephthalic acid in methonol into an esterification reaction zone, and heating the suspension. Since 2,6-naphthalenedicarboxylic acid has a melting point of above 300° C. and decomposes before it is melted, it cannot be fed into an esterification reaction zone in the form of a melt. We therefore attempted to esterify 2,6-naphthalenedicarboxylic acid continuously by feeding a suspension of its solid particles in methanol into a heating zone, as in the case of esterifying terephthalic acid. As a result, we found that at the methyl-esterification temperature of 2,6-NDA, blockage phenomena occurred in reaction vessels and feed lines for the starting suspension within a very short period of time, and the esterification could not be performed smoothly over long periods of time. We assume that this is probably because the rate of esterification reaction of 2,6-NDA is lower than that of terephthalic acid, the 2,6-NDA particles tend to flocculate in the methanol phase, and the solubility of 2,6-NDA in methanol is much lower than that of terephthalic acid in methanol. However, no exact reason has ever been known to us.

We also attempted to perform a method in which 2,6-NDA is suspended in molten 2,6-NDA(CH$_3$)$_2$ and/or esterification intermediate of 2,6-NDA, and the suspension is fed into an esterification reaction zone, and then contacted with methanol separately fed. But as in the case of feeding 2,6-NDA as a suspension in methanol, a blockage phenomenon occurred in feed lines for the raw material, and the esterification reaction could not be performed smoothly for long periods of time.

It is generally accepted that when a sufficient flowing speed is given to solid particles to be conveyed in the form of a suspension, the sedimentation of the particles can be prevented, and thus, the blockage of the flow passage can be obviated. In fact, no blockage phenomenon occurs in the case of a suspension of terephthalic acid in methanol if it is caused to flow at a sufficiently high speed. However, this general theory has been found inapplicable to the feeding of a suspension of solid particles of 2,6-NDA into an esterification reaction zone maintained at the esterification temperature. If, for example, a suspension of 2,6-NDA in methanol is treated at a temperature below the methyl-esterification temperature, for example, at a temperature of below about 130° C., a blockage phenomenon can be avoided by giving a sufficient flowing speed to the suspension, and the above general theory can be applied. However, we found unexpectedly that at a temperature of above about 140° C., not only the blockage phenomenon cannot be substantially prevented at an increased flow rate; but if the flow rate is increased beyond a certain extent, the blockage phenomenon occurs abruptly. It was also found that even if the diameter of the flow path is increased, it can only result in somewhat prolonging the time that elapses until the blockage occurs, and cannot bring about a substantial prevention of the blockage phenomenon.

Further investigations were therefore made into the above blockage phenomenon which occurs in the case of a suspension of 2,6-NDA but does not in the case of a suspension of solid particles of terephthalic acid. This unexpectedly led to the discovery that there is a critical correlation between the above blockage phenomenon and the specific surface area of 2,6-NDA solid particles to be fed as their suspension, for example, in methanol into a reaction zone. We have finally found that when the solid particles of 2,6-NDA have a specific surface area, which can have a relation not merely to their particle size, but also to their density or surface condition, of at least about 4,000 cm$^2$/g, the above disadvantage of blockage phenomenon at the methyl-esterification temperature can be overcome. No reason has yet been able to be assigned to this improvement, but as shown experimentally hereinbelow, the process of this invention enables dimethyl 2,6-naphthalenedicarboxylate to be produced with commercial advantage by a smooth operation over long periods of time.

Accordingly, it is an object of this invention to provide a process for preparing dimethyl 2,6-naphthalenedicarboxylate of superior quality in a good yield, which can eliminate the blockage phenomenon occurring at the time of methyl-esterifying 2,6-naphthalenedicarboxylic acid by feeding a suspension of solid particles of 2,6-NDA in methanol, or molten 2,6-NDA monomethyl or dimethyl ester and/or esterification intermediate of 2,6-NDA into an esterification reaction zone, and enables the reaction to be carried out smoothly over prolonged periods of time.

Other objects and advantages of this invention will become more apparent from the following description and accompanying drawings in which.

According to the process of this invention, solid particles of 2,6-NDA having a specific surface area of at least about 4,000 cm$^2$/g are fed into a reaction zone at an elevated pressure in the presence or absence of an esterification catalyst, and heated at a temperature of about 140° to about 350° C.

The specific surface area, as used in the present application, is a value measured by means of a Blaine air-permeating device.

The 2,6-naphthalenedicarboxylic acid used in the process of this invention may be those prepared by any method of preparation, but is required to have a specific surface area of at least about 4,000 cm$^2$/g as solid particles.

Various methods for preparing 2,6-NDA are known, for example, the oxidation of 2,6-dialkyl naphthalenes, the thermal rearrangement of naphthalenedicarboxylic acid isomers other than its 2,6-isomer, or the thermal disproportionation of naphthoic acid.

The particle diameter of 2,6-NDA differs according to the method of preparation and the conditions for preparation. By selecting the manufacturing conditions, very fine particles having a specific surface area of at least 4,000 cm$^2$/g could be prepared, but usually 2,6-NDA prepared by ordinary methods has a particle diameter of more than 20 microns and a specific surface area of below 2,000 cm$^2$/g.

If the particle size is below 20 microns, a solid-liquid separating operation, such as the separation of 2,6-NDA from the solvent or the washing of the separated 2,6-NDA, becomes difficult in the manufacture of 2,6-NDA. Therefore, the production of 2,6-NDA as fine particles is not preferred in commercial operations. In the present invention, it is preferred to pulverize and sieve 2,6-NDA solid particles having a low surface area prepared by ordinary methods, so that solid particles having a specific surface area of at least about 4,000 cm$^2$/g can be used.

Preferably, the specific surface area of 2,6-NDA solid particles is at least about 8,000 cm$^2$/g, and more preferably, it is at least about 12,000 cm$^2$/g.

There is no particular upper limit to the specific surface area, but in view of the labor and time required for the pulverizing operation, the specific surface area is preferably up to about 100,000 cm$^2$/g.

In the process of this invention, 2,6-NDA solid particles having such a specific surface area are fed into an esterification reaction zone usually as a suspension in methanol or molten dimethyl 2,6-naphthalenedicarboxylate and/or esterification intermediate of 2,6-NDA. The amount of methanol or the molten dimethyl 2,6-naphthalenedicarboxylate and/or esterification intermediate of 2,6-NDA can be one sufficient to form a suspension having flowability. For example, the amount of methanol is 10 to 200 molar times, preferably 15 to 150 molar times, the amount of 2,6-NDA, and the amount of the molten dimethyl 2,6-naphthalenedicarboxylate and/or esterification intermediate of 2,6-NDA is 1 to 100 times, preferably 2 to 9 times, the weight of 2,6-NDA. The dimethyl 2,6-naphthalenedicarboxylate and/or esterification intermediate may be a recycle of the esterification, such as a part of the reaction product as obtained or the residue resulting after separating a part or whole of dimethyl 2,6-naphthalenedicarboxylate from the reaction product by, for example, distillation at reduced pressure. Those separately prepared can also be used; namely, monomethyl and/or dimethyl 2,6-naphthalenedicarboxylate obtained by reacting 2,6-NDA with methanol, and the reaction product of 2,6-NDA and methanol either as such or partly separated.

The esterification reaction can be performed at a temperature of about 140° to about 350° C. When 2,6-NDA solid particles are fed as a suspension in the molten dimethyl 2,6-naphthalenedicarboxylate and/or esterification intermediate of 2,6-NDA, the esterification reaction needs to be carried out at a temperature above the point at which the ester or the esterification intermediate is in the molten state, preferably at a temperature of at least 190° C.

The reaction is carried out at an elevated pressure, usually at about 5 to 200 Kg/cm$^2$·abs., preferably at about 10 to 150 Kg/cm$^2$·abs. The process of this invention can be performed either in the presence or absence of an esterifying catalyst. When no catalyst is used, it is preferred to employ relatively high temperatures, for example, about 240° to about 320° C. Specific examples of such an esterification catalyst are ZnO, ZnCl$_2$, and Co(OCOCH$_3$)$_2$.

The process of this invention easily prevents 2,6-NDA from adhering to, and depositing on, those places where a suspension of 2,6-NDA in methanol or molten dimethyl 2,6-naphthalenedicarboxylate and/or esterification intermediate of 2,6-NDA makes contact with the heated inner wall of flowing passage way or the heated inner wall of the reactor and causes blockage or scales. Accordingly, the esterification can be carried out smoothly and continuously over prolonged periods of time.

The process of this invention can be applied to any type of apparatus for preheating raw materials for esterification and to any type of esterification reaction apparatus, but the advantage of the process of this invention is especially striking when it is used in the case of continuously feeding a suspension of 2,6-NDA in methanol into tubular reactor, and in the case of continuously feeding a suspension of 2,6-NDA in molten dimethyl 2,6-naphthalenedicarboxylate and/or esterification intermediate of 2,6-NDA into a reactor of a plate tower-type or of a stirring vessel-type and contacting it with methanol separately fed.

The following Examples illustrate the present invention in greater detail.

In the Examples, all parts are by weight.

The specific surface area of the solid particles of 2,6-NDA is determined by the following method.

1. Measuring device used

Figure 3:
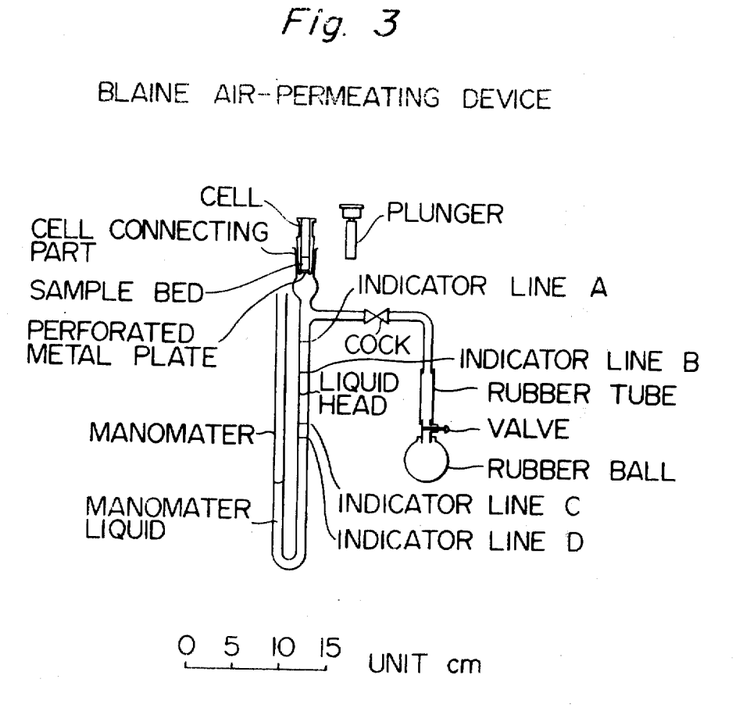
FIG. 3 shows in schematic form a Blaine Air-Permeating device used for measuring the specific surface area of the 2,6-naphthalene dicarboxylic acid used in the process of the present invention.

A Blaine air-permeating device for testing cement as shown in the accompanying FIG. 3 is used.

The specification of the air-permeating device shown in FIG. 3 is as follows:

| | |
|---|---|
| Distance between indicator line A and indicator line B | 40 ± 1 mm |
| Distance between indicator line B and indicator line C | 55 ± 0.2 mm |
| Distance between indicator line C and indicator line D | 15 ± 1 mm |
| Inside diameter of the cell | 12.7 ± 0.7 mm |
| Distance between the upper edge of the cell and the upper edge of the projecting seat | 50 ± 3 mm |
| Difference between the inside diameter of the cell and the outside diameter of the plunger | less than 0.1 mm |
| Width of an air-permeating hole in the side of the plunger | 3 ± 0.5 mm |
| Thickness of the perforated metal plate | 0.9 ± 0.1 mm |
| Difference between the diameter of the perforated metal plate and the inside diameter of the cell | less than 0.5 mm |
| Diameter of the hole | 1 ± 0.2 mm |

The length of the plunger from the undersurface of the collar is such as to make the height of the bed 15 ± 1 mm. The inside surface of the cell is finished by polishing, and the cell and the manometer are brought into contact by grinding. The number of the holes of the perforated metal plate is 25 to 35, and the holes are provided uniformly on the entire surface of the disc.

The filter paper used is one for quantitative analysis, and its size is adjusted to the inside diameter of the cell. The manometer liquid is a non-volatile, non-hygroscopic, low viscosity and low density substance such as dibutyl phthalate or a light mineral oil.

2. Standardization test for the device

A standard sample of cement (No. 101 series standard sample with a known surface area; usually sold as an accessory to an apparatus) is used. The specific gravity of the standard sample is 3.15, and the porosity of the bed is 0.500 ± 0.005. The test method follows the "operation" to be shown in the next paragraph (3) with slight modifications. The measurement is made three or more times with a new bed prepared every time, and then an average value of $t_o$ shown below is calculated.

The standardization test must be performed every time there is the contamination of the manometer liquid or a change in its amount.

3. Operation

About 10 g of a sample is placed in a 100 cc bottle and after sealing, vigorously shaken for about 2 minutes to unravel the sample. Then, the sample is taken out of the bottle and weighed exactly to an amount of 0.005 g in accordance with the following equation.

$$\omega = \rho v(1-e)$$

wherein
- $\omega$: the weight of the sample to be weighed,
- $\rho$: the specific gravity of the sample (3.15 for the standard sample, and 1.478 for 2,6-NDA)
- $v$: the volume (cm³) occupied by the sample bed in the cell (see Note below)
- $e$: the porosity of the sample bed (0.500 ± 0.005 for the standard sample, and 0.55 for 2,6-NDA).

The cell is removed from the manometer, and the perforated metal plate and filter paper and placed accurately at its bottom. The weighed sample is placed thereon, and spread flat by tapping the side of the cell lightly. Another filter paper is placed on the sample, and the plunger is gently pushed. The collar of the plunger is brought into intimate contact with the upper edge of the cell, after which the plunger is gently removed off. Then, the cell is brought into intimate contact with the manometer, and the liquid head within the U-shaped tube is raised to the indicator line A, after which the cock is closed. The time required until the liquid head falls from the indicator line B to the indicator line C is accurately measured to the order of 0.5 second. The specific surface area of the sample is calculated from the following equation.

$$S = S_o \frac{\rho}{\rho} \sqrt{\frac{t}{t_o}} \frac{1-e_o}{\sqrt{e_o^3}} \frac{\sqrt{e^3}}{1-e}$$

wherein
- $S$ is the specific surface area (cm²/g) of the sample;
- $S_o$ is the specific surface area (cm²/g) of the standard sample;
- $t_o$ is the time (seconds) required until the head of the manometer liquid falls from the indicator line B to the indicator line C when the standard sample is used as a bed;
- $t$ is the time (seconds) required until the head of the manometer liquid falls from the indicator line B to the indicator line C when the sample is used as a bed;
- $e_o$ is the porosity (0.500) of the bed of the standard sample;
- $e$ is the porosity (0.55 in the case of 2,6-NDA) of the bed of the sample;
- $\rho_o$ is the specific gravity (3.15) of the standard sample; and
- $\rho$ is the specific gravity (1.478 in the case of 2,6-NDA) of the sample.

The specific surface area test is carried out two or more times with a new bed prepared every time. An average value of two or more replicates having similar values with an error within 2% is determined, and the first place of the integer is rounded to 0. During the test, the sample and the measuring device must be maintained at room temperature, and the temperature should not differ from that used in the standardization test by more than ± 3° C.

Note: Measurement of $v$

The porous metal plate is accurately placed at the bottom of the cell, and two sheets of filter paper are brought into intimate contact with the top surface of the metal plate. The cell is then filled with mercury, and air bubbles adhering to the inside wall of the cell are completely removed. The surface of the mercury is held by a small glass plate to make the level of the mercury surface equal to the upper edge of the cell. Then, the mercury and the filter paper are withdrawn from the cell, and the weight (Wa) of the mercury is measured.

Next, the porous metal plate is accurately placed at the bottom of the cell, and one sheet of filter paper is brought into intimate contact with the metal plate. A suitable amount (usually 2.80 to 3.00 g) of the above standard sample is placed in the cell, and the measuring surface of the cell is tapped lightly to spread the surface of the standard sample flat. Another sheet of filter paper is placed thereon, and compressed gradually by means of the plunger. The sample is gradually compressed, and the weight of the sample is regulated so that the collar of the plunger comes into intimate contact with the upper edge of the cell.

The sample is gradually compressed, and after confirming that the collar of the plunger comes into intimate contact with the upper edge of the cell, the plunger is removed off gradually. The upper side of the bed so prepared is filled with mercury, and the surface of the silver is held by a small glass plate to make the level of the mercury surface equal to the upper edge of the cell. Then, the mercury is withdrawn, and its weight (Wb) is measured.

The volume ($v$) of the bed is calculated from the following equation to the order of 0.005 cm³.

$$v = \frac{W_a - W_b}{d}$$

wherein
- $v$ is the volume (cm³) of the bed,
- $W_a$ is the weight (g) of the mercury filled in the cell without making a bed;
- $W_b$ is the weight (g) of the mercury filled after preparing a bed; and
- $d$ is the density (g/m³) of mercury at the testing temperature.

EXAMPLES 1 TO 4 AND COMPARATIVE EXAMPLES 1 TO 10

Figure 1:
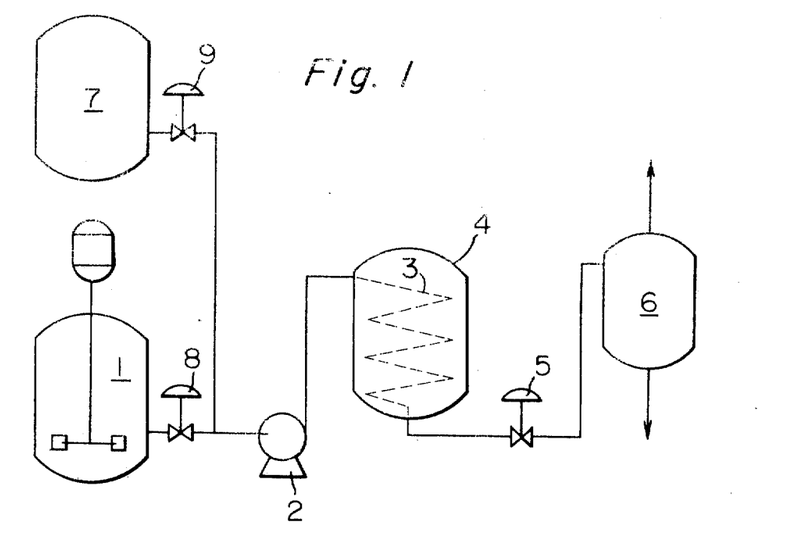
FIG. 1 shows in schematic form a flow sheet of one arrangement of apparatus for carrying out the process of the present invention.

Using an apparatus of the type shown in FIG. 1 of the accompanying drawings, 2,6-NDA solid particles having a specific surface area within and outside the range specified in the present invention were respectively esterified in the absence of an esterifying catalyst. In Comparative Examples 2, 3, 5, 6, 9, and 10, 2,6-NDA solid particles prepared by ordinary methods and having a specific surface area of 1,260 cm²/g were used. In other Comparative Examples and the Examples, the 2,6-NDA solid particles used in Comparative Example 2 were pulverized and sieved to provide the surface areas given in Table 1.

The esterification reaction was carried out in the following manner. Referring to FIG. 1, 2,6-NDA and methanol were placed in a material slurrying tank 1, and well stirred to form a uniform slurry having the 2,6-NDA concentration shown in Table 1. The slurry was fed into a tubular reactor 3 with an inside diameter of 10 mm and a length of 100 m via a switch valve 8 by means of a pressure pump 2. The reactor was set in a heat transfer medium tank 4, and heated by the heat transfer medium. The resulting product withdrawn from the tubular reactor 3 was taken out into a flush tank 6 via a flush valve 5.

When a great pressure drop detected up to the exit of the tubular reactor 3 during the reaction and the tube was somewhat blocked the switch valve 8 was closed, and a switch valve 9 was opened. Thus, methanol stored in a methanol tank 7 was fed into the reactor. When a sign of blockage disappeared, the switch valves 8 and 9 were again operated, and the starting slurry was fed into the reactor.

The operating conditions and the results are shown in Table 1.

The above procedure was repeated except that a suspension of isophthalic acid in methanol, a suspension of terephthalic acid in methanol, and a suspension of 2-methylterephthalic acid in methanol were used respectively instead of the 2,6-NDA suspension. The results are shown in Table 1'.

It can be seen from these comparisons that with these aromatic carboxylic acids, no problem of blockage arose.

Table 1

| Example (Ex.) and Comparative Example (Comp.) | Specific surface area of 2,6-NDA solid particles (cm²/g) | Concentration of 2,6-NDA in methanol suspension (wt. %) | Temperature of heat transfer medium (° C) | Reaction pressure (Kg/cm²) | Rate of feeding the starting slurry (l/hr) | Time which elapsed until a blockage phenomenon first occurred after the feeding of the slurry (minutes) | Result of operation for 7 consecutive days in accordance with a cycle of feeding the slurry for 7.5 hrs and methanol for 0.5 hr |
|---|---|---|---|---|---|---|---|
| Ex. 1 | 4500 | 20 | 260 | 120 | 20 | >450 | Operable smoothly |
| Comp. 1 | 3800 | " | " | " | " | 180 | Inoperable 1) |
| Comp. 2 | 1260 | " | " | " | " | 20 | Inoperable 2) |
| Comp. 3 | 1260 | " | 130 | " | " | >450 | Esterification scarcely occurred |

Table 1-continued

| Example (Ex.) and Comparative Example (Comp.) | Specific surface area of 2,6-NDA solid particles (cm²/g) | Concentration of 2,6-NDA in methanol suspension (wt. %) | Temperature of heat transfer medium (° C) | Reaction pressure (Kg/cm²) | Rate of feeding the starting slurry (l/hr) | Time which elapsed until a blockage phenomenon first occurred after the feeding of the slurry (minutes) | Result of operation for 7 consecutive days in accordance with a cycle of feeding the slurry for 7.5 hrs and methanol for 0.5 hr |
|---|---|---|---|---|---|---|---|
| Ex. 2 | 4500 | 20 | 260 | 120 | 50 | >450 | Operable smoothly |
| Comp. 4 | 3800 | " | " | " | " | 90 | Inoperable 3) |
| Comp. 5 | 1260 | " | " | " | " | 10 | Inoperable 4) |
| Comp. 6 | 1260 | " | 130 | " | " | >450 | Esterification scarcely occurred |
| Ex. 3 | 4500 | 10 | 260 | 120 | 20 | >450 | Operable smoothly |
| Ex. 4 | " | " | " | " | 50 | >450 | Operable smoothly |
| Comp. 7 | 3800 | 10 | 260 | 120 | 20 | 270 | Inoperable 5) |
| Comp. 8 | 3800 | " | " | " | 50 | 150 | Inoperable 6) |
| Comp. 9 | 1260 | 10 | 260 | 120 | 20 | 30 | Inoperable 7) |
| Comp. 10 | 1260 | " | " | " | 50 | 20 | Inoperable 8) |

Notes:
1) When the operation was performed in accordance with a cycle of feeding the starting slurry for about 180 minutes, immediately then stopping the feeding of the slurry and feeding methanol for 30 minutes from the methanol tank, and then feeding the starting slurry for 120 minutes, it was feasible until the end of the fifth cycle. However, when the sixth cycle was begun and the material slurry was fed, a complete blockage occurred in about 30 minutes.
2) In 20 minutes, a blockage phenomenon occurred. Immediately then, the feeding of the slurry was stopped and methanol was fed, but the equipment still remained blocked.
3) In about 90 minutes, a blockage of phenomenon occurred. Immediately then, the feeding of the slurry was stopped, and the operation was performed in accordance with a cycle of feeding methanol for 30 minutes and then feeding the starting slurry for 60 minutes. The operation was feasible until the end of the third cycle, but in 20 minutes after the beginning of the fourth cycle, a complete blockage occurred.
4) In 10 minutes, a blockage phenomenon occurred. Immediately then, the feeding of the slurry was stopped, and methanol was fed for 30 minutes. Then, the feeding of the starting slurry was resumed, but in about 5 minutes, a complete blockage occurred.
5) In about 270 minutes a blockage phenomenon occurred, and immediately then, the feeding of the starting slurry was stopped. Then, the operation was performed in accordance with a cycle of feeding methanol for 30 minutes and then feeding the starting slurry for 240 minutes. The operation was feasible until the end of the sixth cycle, but in 15 minutes after the beginning of the seventh cycle, a complete blockage occurred.
6) In about 150 minutes, a blockage phenomenon occurred, and immediately then, the feeding of the starting slurry was stopped. Then, the operation was performed in accordance with a cycle of feeding methanol for 30 minutes and then feeding the starting slurry for 120 minutes. The operation was feasible until the end of the fourth cycle, but in 35 minutes after the beginning of the fifth cycle, a complete blockage occurred.
7) In about 30 minutes, a blockage phenomenon occurred. Immediately then, the feeding of the slurry was stopped. Then, methanol was fed for 30 minutes, and again, the slurry was fed. But in about 10 minutes, a complete blockage occurred.
8) In about 20 minutes, a blockage phenomenon occurred. Immediately then, the feeding of the slurry was stopped, and methanol was fed for 30 minutes. Again, the starting slurry was fed, but in about 10 minutes, a complete blockage occurred.

Table 1'

| Run No. | Solid particles of aromatic carboxylic acids | | Concentration of the aromatic carboxylic acid in the methanol slurry (wt. %) | Temperature of heat medium (° C) | Reaction pressure (Kg/cm²) | Flow rate of the slurry (l/hr) | Presence of a blockage phenomenon after 4320 minutes |
|---|---|---|---|---|---|---|---|
| | Type | Specific surface area (cm²/g) | | | | | |
| 1 | Isophthalic acid | 960 | 20 | 260 | 120 | 20 | None |
| 2 | Isophthalic acid | 960 | 30 | 260 | 120 | 20 | None |
| 3 | Terephthalic acid | 840 | 20 | 260 | 120 | 20 | None |
| 4 | 2-Methyl- | | | | | | |

Table 1'-continued

| Run No. | Solid particles of aromatic carboxylic acids | | Concentration of the aromatic carboxylic acid in the methanol slurry (wt. %) | Temperature of heat medium (° C) | Reaction pressure (Kg/cm²) | Flow rate of the slurry (l/hr) | Presence of a blockage phenomenon after 4320 minutes |
|---|---|---|---|---|---|---|---|
| | Type | Specific surface area (cm²/g) | | | | | |
| | terephthalic acid | 1380 | 20 | 260 | 120 | 20 | None |

EXAMPLES 5 TO 11 AND COMPARATIVE EXAMPLES 11 AND 12

The same 2,6-NDA as used in Comparative Example 2 (with a surface area of 1260 cm²/g) was pulverized and sieved to prepare 2,6-NDA solid particles with varying specific surface areas. These 2,6-NDA solid particles were esterified in the same esterifying apparatus as in Example 1. The treating conditions and the conversion of 2,6-NDA to its ester are shown in Table 2.

Table 2

| Example (Ex.) and Comparative Example (Comp.) | Specific surface area of 2,6-NDA solid particles (cm²/g) | Concentration of 2,6-NDA in the methanol slurry (wt. %) | Temperature of heat transfer medium (° C) | Reaction pressure (Kg/cm² . G) | Flow rate of the starting slurry (l/hr) | Average degree of esterification of 2,6-NDA (mol %) |
|---|---|---|---|---|---|---|
| Comp.11 | 2500 | 20 | 260 | 130 | 20 | — |
| Comp.12 | 3800 | 20 | 260 | 130 | 20 | 67 |
| Ex. 5 | 4500 | 20 | 260 | 130 | 20 | 72 |
| Ex. 6 | 8600 | 20 | 260 | 130 | 20 | 74 |
| Ex. 7 | 12700 | 20 | 260 | 130 | 20 | 80 |
| Ex. 8 | 81000 | 20 | 260 | 130 | 20 | 81 |
| Ex. 9 | 12700 | 30 | 260 | 130 | 20 | 77 |
| Ex. 10 | 12700 | 20 | 235 | 80 | 10 | 68 |
| Ex. 11 | 12700 | 20 | 260 | 130 | 10 | 88 |

In Comparative Example 11, the equipment tended to be blocked in about 60 minutes after the feeding of the starting slurry. Therefore, the feeding of the slurry was stopped, and methanol was fed for 30 minutes, and then again the slurry was fed. But in about 40 minutes from then, the equipment was again blocked, and therefore, the reaction was stopped.

In Comparative Example 12, the equipment tended to be blocked in about 180 minutes after the feeding of the starting slurry. Therefore, the operation was performed in accordance with a cycle of feeding methanol for 30 minutes, and then feeding the starting slurry for 120 minutes. This cycle could be repeated five times, but in about 30 minutes after the beginning of the sixth cycle, a blockage phenomenon again occurred.

In Example 5, the operation was performed in accordance with a cycle of feeding the starting slurry for 450 minutes, and then feeding methanol for 30 minutes. After operating for 7 consecutive days, no blockage occurred, but the operation could be performed smoothly.

In Example 6, the operation was performed in accordance with a cycle of feeding the starting slurry for 1410 minutes and then feeding methanol for 30 minutes. After operating for 7 consecutive days, no blockage occurred, but the operation could be performed smoothly.

In Examples 7 to 11, the starting slurry alone was fed continuously, but no blockage occurred after operating for 4320 minutes.

EXAMPLES 12 TO 19 AND COMPARATIVE EXAMPLES 13 TO 15

Figure 2:
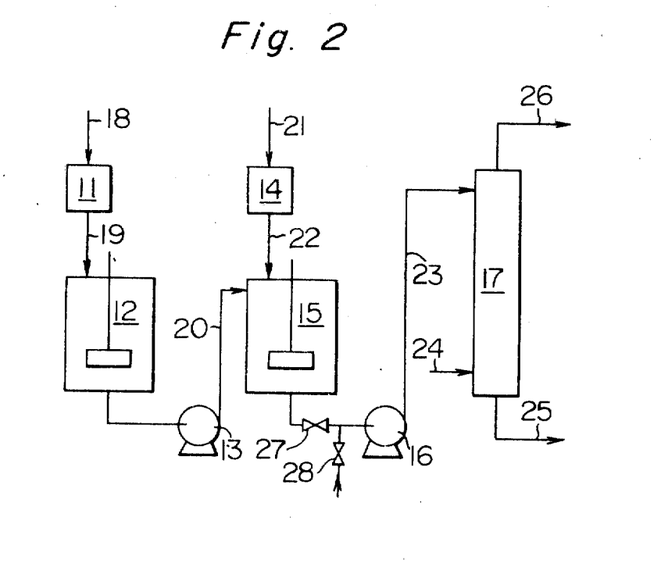
FIG. 2 shows in schematic form a flow sheet of another arrangement of apparatus for carrying out the process of the present invention.

Methyl-esterification of 2,6-naphthalenedicarboxylic acid was performed continuously using an apparatus of the type shown in FIG. 2 of the accompanying drawings.

Referring to FIG. 2, dimethyl 2,6-naphthalenedicarboxylate and/or an esterification intermediate of 2,6-NDA were fed from an inlet port 18 into a melting device 11, and melted there. The molten product was introduced into a melt storing tank by means of a conduit 19. The melt stored in the storage tank 12 was quantitatively introduced into a material preparation tank 15 through a conduit 20 by means of a metering pump 13. 2,6-NDA was charged into a storage tank 14 from a charge opening 21, and stored there. From the storage tank 14, 2,6-NDA was quantitatively introduced into the material preparing tank 15 by means of a screw feeder 22. In the material preparation tank 15, the 2,6-NDA was contacted with the melt at the temperatures shown in Table 4. Then, the mixture was introduced into an esterification reaction apparatus 17 through a conduit 23 by means of a metering pump 16. When blockage occurred owing to a solid matter in the material feeding system, a valve 27 was closed, and a valve 28 was opened to introduce high pressure N₂ gas into the feed system, and thus to blow away the adhering solid matter into the reactor.

After removing the adhering solid matter causing the blockage by means of nitrogen gas blow, the valve was returned to the original condition, and the esterification reaction was again performed.

Heated methanol gas was quantitatively introduced into the lower part of the esterification reaction apparatus 17 through a conduit 24 so as to perform the esterification. The unreacted methanol, the water and vaporous esterified product generated by the reaction were withdrawn from the top of the esterification reactor 17 through a line 26 so that the pressure in the reactor was maintained constant. From the lower part of the reactor, the esterification reaction product in the molten state was withdrawn through a conduit 25 so that the liquid level at the bottom of the reactor became constant.

The results of the esterification reaction are shown in Table 4 below.

Especially when the specific surface area was at least 8,000 cm²/g, the operation could be performed almost without blowing away the adhering solid matter by introducing high pressure nitrogen gas. When the specific surface area was above 12,000 cm²/g, the operation could be continued smoothly without any introduction of pressurized nitrogen gas.

Examples 12 to 15 cover the case of using a bubble-tower type reactor; Example 16, the case of using a porous plate tower-type reactor; and Examples 17 to 19, the case of using a reactor equipped with a stirring tank. In all of these Examples, the operation could be Table 4-(1)

|  | Unit | Ex. 12 | Ex. 13 | Ex. 14 | Ex. 15 |
|---|---|---|---|---|---|
| Specific surface area of | cm²/g | 4,500 | 8,600 | 12,700 | 81,000 |
| Concentration of 2,6-NDA in the starting material mixture | % | 30 | 30 | 30 | 30 |
| Feeding temperature of the starting material mixture | °C | 260 | 260 | 260 | 260 |
| Feed rate of the starting material mixture | parts/hr. | 2 | 2 | 2 | 2 |
| Rate of feeding methanol into the esterification reactor | parts/hr. | 2 | 1 | 2 | 4 |
| Type of the reactor | — | Bubble tower type | " | " | " |
| Inside temperature of the reactor | °C | 280 | 280 | 280 | 280 |
| Inside pressure of the reactor | Kg/cm²G | 30 | 30 | 30 | 30 |
| Results obtained after operating for 74 hrs. continuously | — | Operable; 6 N₂ blowings | Operable; 1 N₂ blowing | Operable; no N₂ blowing | Same as Ex. 14 |
| Average conversion of 2,6-NDA | mol % | 94 | 90 | 95 | 96 |

Table 4-(2)

|  | Ex. 16 | Ex. 17 | Ex. 18 | Ex. 19 | Comp. 13 | Comp. 14 | Comp. 15 |
|---|---|---|---|---|---|---|---|
| Specific surface of the starting 2,6-NDA | 12,700 | 12,700 | 12,700 | 12,700 | 2,500 | 3,800 | 3,800 |
| Concentration of 2,6-NDA in the starting material mixture | 20 | 20 | 20 | 20 | 20 | 20 | 20 |
| Feeding temperature of the starting material mixture | 230 | 200 | 195 | 300 | 260 | 260 | 260 |
| Feed rate of the starting material mixture | 1 | 2 | 2 | 2 | 2 | 2 | 4 |
| Rate of feeding methanol into the esterification reactor | 2 | 2 | 2 | 1 |  | 2 | 2 |
| Type of the reactor | Porous plate tower-type | Stirring tank-type | " | " | bubble tower-type | " | " |
| Inside temperature of the reactor | 290 | 260 | 260 | 300 | 260 | 260 | 260 |
| Inside pressure of the reactor | 20 | 40 | 40 | 20 | 30 | 30 | 30 |
| Results obtained after operating for 72 hrs. continuously | Operable; no N₂ blowing | Operable; no N₂ blowing | Operable; 3 N₂ blowing | Operable; no N₂ blowing | The conduits blocked in 8 hours after start of operation, and the operation failed; 10 N₂ blowings | The conduits blocked in 20 hours after start of operation, and the operation failed; 18 N₂ blowings | The conduits blocked in 12 hours after start of operation, and the operation failed; 15 N₂ blowings |
| Average conversion of 2,6-NDA | 92 | 85 | 84 | 96 | — | — | — |

As shown in Examples 12 to 19, when the specific surface area of 2,6-NDA was at least 4,000 cm²/g, the operation was continuously feasible for 72 hours, and essentially, the operation would be able to be performed for longer periods of time in good condition.

performed continuously for prolonged periods of time.

In Example 18, the temperature of the starting mixture being fed was 195° C., and nitrogen gas blowing had to be performed three times during a 72-hour continuous operation. But this did not substantially impede the operation.

In Examples 17 and 19, the temperature of the starting feed mixture was above 200° C. In this case, the operation could be performed without any blowing of nitrogen gas.

As shown in Comparative Examples 13 and 14, when the specific surface area of 2,6-NDA was lower than 4,000 cm²/g, the operation could be performed only for less than 24 hours even when the solid matter causing blockage was removed by nitrogen blowing.

The results of Comparative Example 15 show that even when the flow rate of the starting mixture is increased, the failure of operation begins at an earlier time.

What we claim is:

1. A process for preparing dimethyl 2,6-naphthalenedicarboxylate, which comprises continuously esterifying 2,6-naphthalenedicarboxylic acid with methanol at a temperature of about 140° to 350° C. in the presence or absence of an esterifying catalyst, said 2,6-naphthalenedicarboxylic acid being fed into an esterification reaction zone in the form of solid particles having a specific surface area of from about 4,000 cm²/g to about 100,000 cm²/g.

2. The process of claim 1 wherein said esterification reaction is carried out in the absence of an esterifying catalyst at a temperature of about 240° to about 320° C.

3. The process of claim 1 wherein said esterification reaction is carried out in a tubular reactor.

4. The process of claim 1 wherein said esterification reaction is carried out in a plate tower-type reactor or a stirring tank-type reactor.

5. The process of claim 1 wherein said 2,6-naphthalenedicarboxylic acid solid particles have a specific surface area of at least about 8000 cm²/g.

6. The process of claim 1 wherein said 2,6-naphthalenedicarboxylic acid solid particles have a specific surface area of at least about 12,000 cm²/g.

7. The process of claim 1 wherein the amount of methanol is 10 to 200 molar times the amount of 2,6-naphthalenedicarboxylic acid.

* * * * *